United States Patent
Vaithiyanathan et al.

(10) Patent No.: US 10,266,481 B2
(45) Date of Patent: Apr. 23, 2019

(54) ORGANOCATALYTIC ASYMMETRIC SYNTHESIS OF ANTIDEPRESSANTS

(71) Applicant: COUNCIL OF SCIENTIFIC & INDUSTRIAL RESEARCH, New Delhi (IN)

(72) Inventors: Venkataramasubramanian Vaithiyanathan, Maharashtra (IN); Rupali Gundappa Kalshetti, Maharashtra (IN); Sudalai Arumugam, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 17 days.

(21) Appl. No.: 15/320,483

(22) PCT Filed: Jun. 22, 2015

(86) PCT No.: PCT/IN2015/050048
§ 371 (c)(1),
(2) Date: Dec. 20, 2016

(87) PCT Pub. No.: WO2015/193921
PCT Pub. Date: Dec. 23, 2015

(65) Prior Publication Data
US 2017/0158607 A1   Jun. 8, 2017

(30) Foreign Application Priority Data

Jun. 20, 2014 (IN) .......................... 1658/DEL/2014

(51) Int. Cl.
| | | |
|---|---|---|
| *C07C 209/68* | (2006.01) | |
| *C07C 211/28* | (2006.01) | |
| *C07C 211/29* | (2006.01) | |
| *C07C 211/38* | (2006.01) | |
| *C07C 269/06* | (2006.01) | |
| *C07C 271/12* | (2006.01) | |
| *C07C 271/14* | (2006.01) | |
| *C07C 271/18* | (2006.01) | |

(52) U.S. Cl.
CPC .......... *C07C 209/68* (2013.01); *C07C 269/06* (2013.01); *C07C 271/12* (2013.01); *C07C 271/14* (2013.01); *C07C 271/18* (2013.01); *C07B 2200/07* (2013.01); *C07C 2602/10* (2017.05)

(58) Field of Classification Search
CPC ... C07C 209/68; C07C 269/06; C07C 271/14; C07C 271/18; C07C 271/12; C07C 249/02; C07C 251/20; C07B 2200/07
See application file for complete search history.

(56) References Cited

U.S. PATENT DOCUMENTS 6,593,496 B1 * 7/2003 Quallich .............. C07C 249/02
                                                564/270
2002/0013337 A1   1/2002 Perros et al.

FOREIGN PATENT DOCUMENTS

WO   2008/009275 A1   1/2008

OTHER PUBLICATIONS

Lee et al. "Stereoselective Amination of Chiral Benzylic Ethers Using Chlorosulfonyl Isocyanate: Total Synthesis of (+)-Sertraline." J. Org. Chem. 2011, 76, 10011-10019 (Year: 2011).*
Chandrasekhar et al. "An Expedient Total Synthesis of cis-(+)-Sertraline from D-Phenylglycine." Tetrahedron 2000, 56, 1111-1114. (Year: 2000).*
Fustero et al. "Asymmetric Allylation/Ring Closing Metathesis: One-Pot Synthesis of Benzo-fused Cyclic Homoallylic Amines. Application to the Formal Synthesis of Sertraline Derivatives." Org. Lett. 2013, 15, 3770-3773. (Year: 2013).*
Chandrasekhar et al., "An Expedient Total Synthesis of cis-(+)-Sertraline from D-Phenylglycin", Tetrahedron, 2000, vol. 56, pp. 1111-1114.
Davis et al., "Asymmetric Synthesis of trans-2,5-Disbustituted Pyrrolidines from Enantiopure Homoallylic Amines. Synthesis of Pyrrolidine (−)-197B", J. Org. Chem., 2006, vol. 71, pp. 2779-2786.
Fustero et al., "Asymmetric Allylation/Ring Closing Metathesis: One-Pot Synthesis of Benzo-fused Cyclic Homoallylic Amines. Application to the Formal Synthesis of Sertraline Derivatives", Organic Letters, 2013, vol. 15, No. 14, pp. 3770-3773.
Kruger et al., "Studies Directed Toward the Synthesis of Viridenomycin. Route 1: Assembly of Three Advanced Intermediates", Tetrahedron Letters, 2001, vol. 42, pp. 4301-4304.

(Continued)

*Primary Examiner* — Amanda L Aguirre
(74) *Attorney, Agent, or Firm* — Baker & Hostetler LLP

(57) ABSTRACT

The present invention relates to a short enantioselective synthesis of 1-amino aryl tetraline compounds of Formula 1 via nucleophilic enamine catalysis using organocatalyst such as proline.

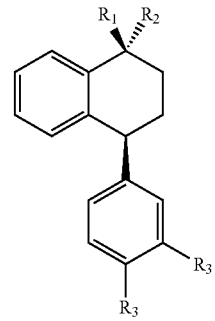

wherein $R_1$ and $R_2$ represent independent of each other hydrogen, (un)substituted or substituted amine;
$R_3$ and $R_4$ represent independent of each other hydrogen or halogen.

4 Claims, 2 Drawing Sheets

(56) References Cited

OTHER PUBLICATIONS

Lee et al.,"Steroselective Amination of Chiral Benzylic Ethers Using Chlorosulfonyl Isocyanate: Total Synthesis of (+)-Sertraline", The Journal of Organic Chemistry, 2011, vol. 76, pp. 10011-10019.
Liu et al., "Discovery of a Novel CCR5 Antagonist Lead Compound Through Fragment Assembly", Molecules, 2008, vol. 13, No. 10, pp. 2426-2441.
Mirafzal et al., "Hole Transfer Promoted Hydrogenation: One-Election Oxidation as a Strategy for Selective Reduction of $\pi$-Bonds", J. Am. Chem., Soc., 1993, vol. 115, pp. 6072-6077.
Toujas et al., "Organometallic Additions to ß-substituted N-Boc-ß-aminoaldehydes: a New Synthesis of Enantiomerically Pure 1,3-disbustituted N-Boc-1,3-aminoalcohols", Tetrahedron, 2000, vol. 56, pp. 2665-2672.
Chandrasekhar et al., "Asymmetric Synthesis of Aza-Diospongin a as an iNOS Inducer", Tetrahedron: Asymmetry, 2009, vol. 20, pp. 2216-2219.

\* cited by examiner

ORGANOCATALYTIC ASYMMETRIC SYNTHESIS OF ANTIDEPRESSANTS

CROSS REFERENCE TO RELATED APPLICATIONS

This application is a National Stage of International Application no. PCT/IN2015/050048, filed on Jun. 22, 2015, which claims priority to Indian patent application no. 1658/DEL/2014, filed on Jun. 20, 2014, the disclosures of which are incorporated by reference in their entirety.

FIELD OF THE INVENTION

The present invention relates to a short, organocatalytic asymmetric enantioselective synthesis of 1-amino aryl tetralin compound of Formula 1 via nucleophilic enamine catalysis using organocatalyst such as proline. Particularly, present invention relates to 1-amino aryl tetralin compound of Formula 1 with high therapeutic value as antidepressants.

BACKGROUND AND PRIOR ART OF THE INVENTION

Proline and its derivatives are useful for the catalytic activation of carbonyl compounds, via nucleophilic enamine catalysis. Several important carbon-carbon bond forming reactions including the Mannich and Michael reactions have been developed using this approach.

List et al showed the proline catalyzed Mannich reaction of acetaldehyde to yield β-aminoaldehydes in high ees, which are desirable products as drug intermediates and in the synthesis of other biologically active molecules.

Compounds with amine functionality at the C-1 position of an indane or tetraline framework have received considerable attention as potential medical agents because of their interesting pharmacological properties.

(+)-Sertraline and Tametraline are the class of 1-amino-aryltetralins most of which have anti depressant activity, especially (+)-sertraline is a potent competitive selective serotinin reuptake inhibitor, which has become a commonly prescribed pharmaceutical for the treatment of depression and other anxiety related disorders. In 2004, it was the ninth top selling drug worldwide, also has become a popular target for asymmetric synthesis due to its small but challenging structure.

Tametraline, a catecholamine reuptake inhibitor, is the parent of a series of chemical compounds investigated by Pfizer that eventually led to the development of sertraline.

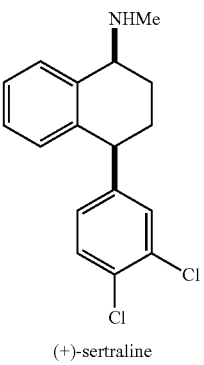

(+)-sertraline

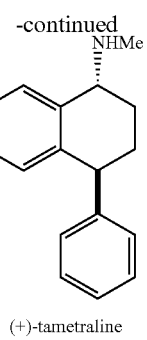

(+)-tametraline

Many reports are available for the synthesis of (+)-sertraline due to its high pharmaceutical importance as a drug.

In an article by Welch et al in J. Med. Chem. 1984, 27, 1508, is disclosed synthesis of racemic sertraline.

According to the procedure, α,β-unsaturated ester was prepared by base catalyzed Stobbe condensation of 3,4-dichlorobenzophenone with diethylsuccinate. Ester was then subjected to acid-catalyzed decarboxylation, followed by catalytic hydrogenation (5% Pd/C) to give the saturated acid. Acid underwent cyclization under Friedel-Crafts' condition (anhyd. $AlCl_3$) to produce tetralone. Finally, reductive amination of tetralone with methylamine ($MeNH_2$, $TiCl_4$; $NaBH_4$, MeOH) afforded (+)-sertraline 1.

Chandrashekar et al. in Tetrahedron, 2000, 56, 1111 have disclosed the synthesis of (+)-sertraline (1a) by employing chiral pool strategy. Thus, reduction of ester with $LiAlH_4$ gave alcohol, which was oxidized to aldehyde under Swern's conditions. Aldehyde on subsequent treatment with Wittig reagent namely $PPh_3=CHCO_2Et$ to afforded α,β-unsaturated ester in 72% yield. The complete reduction of α,β-unsaturated ester gave the saturated alcohol. Oxidation of alcohol with Corey's reagent (PCC) followed by its treatment with Grignard reagent, i.e 3,4-dichlorophenyl-magnesium bromide, gave the secondary alcohol in 83% yield. Alcohol was cyclized intramolecularly with anhyd. $AlCl_3$, which generated with a second chiral centre of separable diastereomers. The conversion of cis isomer to (+)-sertraline (1a) was achieved via a known series of reactions namely debenzylation, Boc-protection, N-methylation and Boc-deprotection. Zhao et. al in Tetrahedron: Asymmetry, 2006, 17, 2074 approach (2006) discloses synthesis of racemic sertraline comprising subjecting racemic (±)-tetralone to reduction using L-proline derived catalyst and $Me_2S.BH_3$ to give diastereomers which were readily separated. The oxidation of trans isomer with PCC gave the optically active (+)-tetralone, which was transformed to (+)-sertraline via reductive amination.

($MeNH_2$, $TiCl_4$, Raney-Ni) Chen et al. on Org. Lett. 1999, 1, 293 have achieved the synthesis of (+)-sertraline by the addition of Grignard reagent onto α,β-unsaturated chiral carbamate to provide in 90% yield. Reductive removal of chiral auxiliary in using NaBH4 in THF-H2O gave alcohol. Alcohol was transformed to iodoaldehyde in 85% yield. Iodoaldehyde on treatment with methylamine gave the corresponding imine which was subjected to BuLi-mediated intramolecular ring closing so that a single diastereomer of (+)-sertraline (1a) was obtained Lautens et al. in J. Am. Chem. Soc. 2005, 127, 15028. have reported the synthesis of (+)-sertraline (1) by employing Diels-Alder reaction between benzenediazonium-2-carboxylate, a benzyne-equivalent and dienyl ester in 1,2-dichloroethane as solvent at 60° C., to give the cycloadduct in 78% yield. Cycloadduct was hydrogenated and the benzyl group deprotected in one-pot using 10% Pd/C and $H_2$ (4 atm) to give acid. The acid was then subjected to Curtius rearrangement via the initial formation of acylazide ($ClCO_2Et$, then $NaN_3$) followed by the addition of allyl alcohol at 90° C., which afforded allyl carbamate. N-methylation and deprotection of allyl group in resulted in the formation of (+)-sertraline 1.

U.S. Pat. No. 6,593,496 relates to a process for preparing the (+) enantiomer of N-[4(3,4-dichlorophenyl)-3,4-dihydro-1(2H)-naphthalenylidene]methanamine by reacting the (+) enantiomer of 4-(3,4-dichlorophenyl)-3,4-dihydro-1 (2H)-naphthalenone with monomethylamine and titanium chloride or molecular sieves.

U.S. Pat. No. 4,536,518 disclose the synthesis of cis (1S,4S)-sertraline which includes condensation of 4-(3,4-dichlorophenyl)-3,4-dihydro-1(2H)-napthalenone with monomethylamine catalysed by $TiCl_4$.

US2007260090 relates to a process for highly stereoselective synthesis of sertraline and sertraline intermediate. The mixture of 4-(3,4-Dichlorophenyl)-3,4-dihydro-N-methyl-1(2H)-naphthalenimine, 5% $Pd/CaCO_3$, water and methanol was taken in a hydrogenation flask and then subjected to hydrogenation under a hydrogen pressure of 0.5 Kg at 20-35 DEG C. for 3 hours 30 minutes. The catalyst was removed by filtration and the solvent evaporated to obtain cis-(+−)-4-(3,4-dichlorophenyl)-1,2,3,4-tetrahydro-N-methyl-naphthalen amine. (trans-(+−): 0.2). It is further disclosed that resolution of the racemic mixture was carried using D(−)mandelic acid to obtain cis-isomer.

The processes described in the art are lengthy, employ large amount of chemicals, additional step of resolution and expensive transition catalysts, often resulting in poor product selectivities which make the processes industrially not feasible.

Hence, there remains a need in the art to develop a concise, cost effective route for synthesis of amino aryl tetralines viz. (+)-sertraline and tametraline with excellent enantioselectivity.

OBJECTIVE OF THE INVENTION

Main object of the present invention to provide a short, cost effective process for synthesis of 1-amino aryl tetralin compound of formula I with excellent enantioselectivity.

Another object of the present invention is to provide synthesis of 1-amino aryl tetralin compound of formula I using cheap and commercially available organocatalyst such as D or L proline.

SUMMARY OF THE INVENTION

Figure 1:
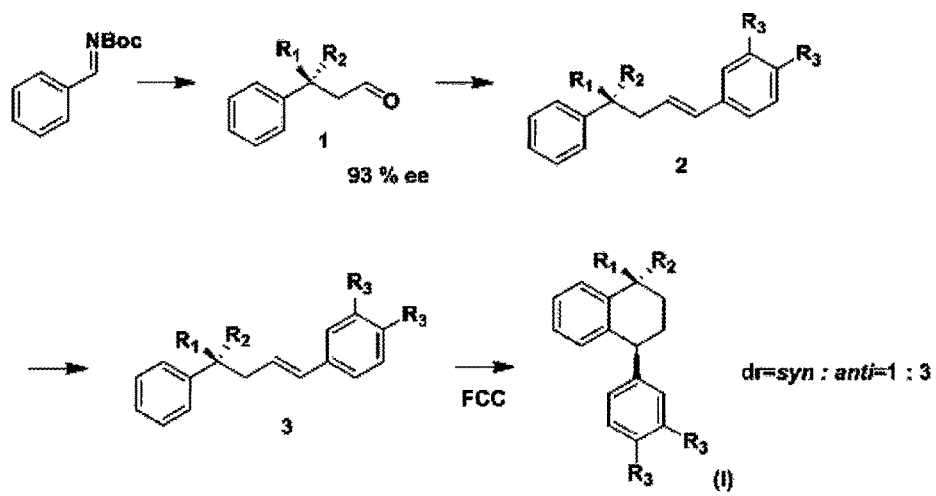
FIG. 1 represents enantioselective synthesis of anti-depressants 1-amino aryl tetralin compound of Formula (I).
Figure 2:
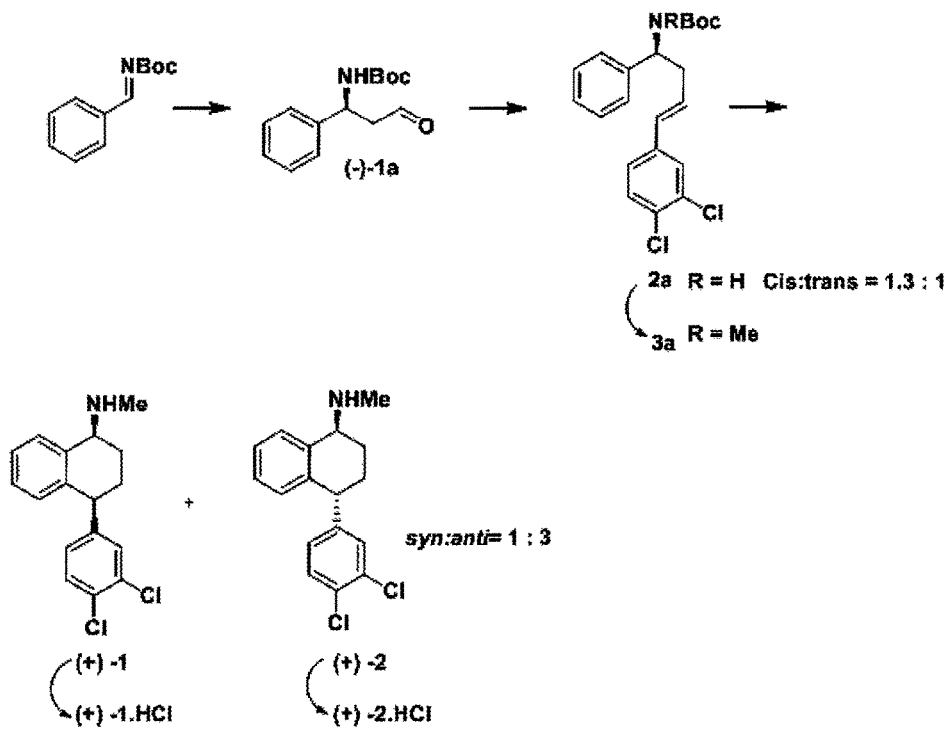
FIG. 2 represents synthesis of (+) sertraline.
Figure 3:
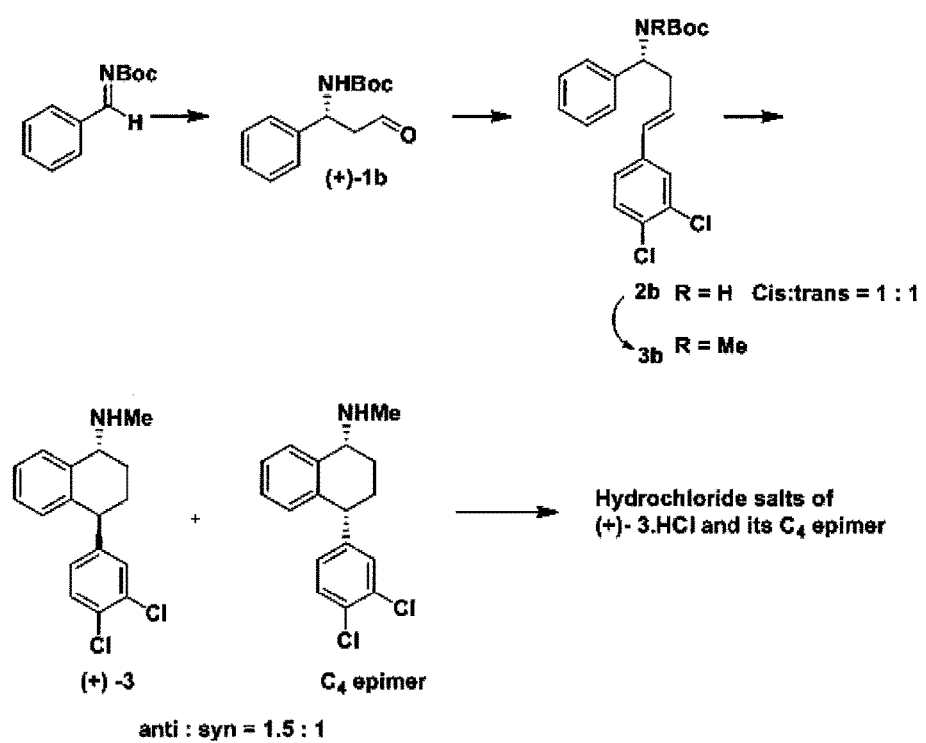
FIG. 3 represents synthesis of (+)-tametraline.

Accordingly, present invention provides a process for the enantioselective synthesis of 1-amino aryl tetralin compound of Formula (I)

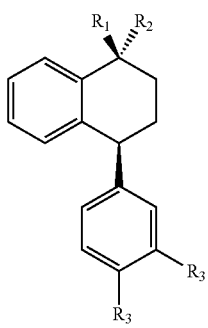

wherein
$R_1$ and $R_2$ represent independent of each other hydrogen, (un)substituted or substituted amine;
$R_3$ and $R_4$ represent independent of each other hydrogen or halogen;
comprising;

a. reacting aryl N-Boc-imine with an aldehyde in presence of D or L-proline to obtain compound 1;

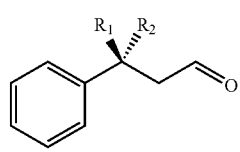

b. reacting compound 1 with triphenyl phosphonium salt in presence of n-butyl lithium or $^tBuOK$ in dry THF to obtain olefinic carbamate (2);

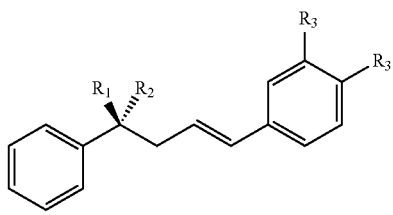

c. alkylating olefinic carbamate (2) in presence of alkyl halide and NaH at 0 to 10° C. to obtain compound (3); and

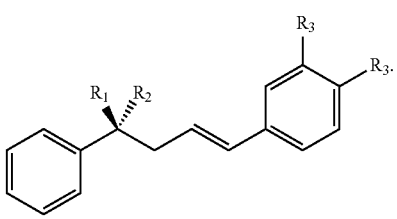

d. deprotecting the N-boc group followed by intramolecular FCC in presence of acid to afford desired compound of formula I.

In an embodiment of the present invention, representative compound of formula I comprising (+) sertraline and (+) tametraline.

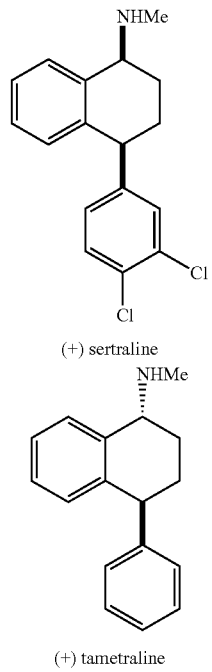

(+) sertraline (+) tametraline

In yet another embodiment, present invention provides a process for the preparation of (+) sertraline with ee>95%

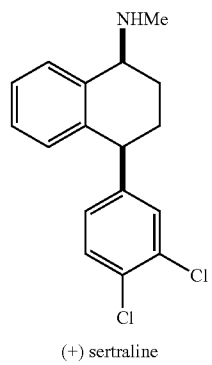 [SMILES: CN[C@H]1CC[C@@H](c2ccc(Cl)c(Cl)c2)c2ccccc21]

(+) sertraline comprising the steps of:
a. reacting N-Boc-benzaldiimine with acetaldehyde in presence of L-proline to obtain (−)β-amino aldehyde (1a);

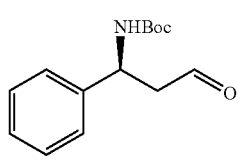

b. treating (−) β-amino aldehyde (1a) with semistabilized 3,4-dichlorobenzyl phosphorous ylide obtained in-situ in presence of base to yield carbamate (2a);

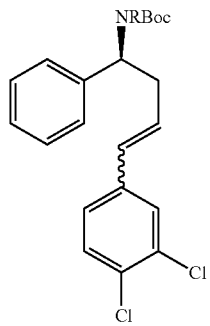

c. methylating carbamate (2a) using methyl iodide and NaH at 0 to 10° C. to obtain N-methylated olefin (3a);

d. deprotecting the Boc group followed by intramolecular FCC of N-methylated olefin in presence of polyphosphoric acid in solvent under reflux condition to obtain mixture of (+) sertraline and its C4-epimer (−)-2 with syn:anti ratio of 1:3;

e. separating (+) sertraline and its C4-epimer (−)-2 through coloumn chromatography followed by converting to their hydrochloride salts respectively.

In yet another embodiment, present invention provides a process for the preparation of (+)-tametraline with ee>95% comprising the steps of:

a. reacting N-Boc-benzaldiimine with acetaldehyde in presence of D-proline to obtain (+) β-amino aldehyde (1b);

b. treating (+) β-amino aldehyde (1b) with semistabilized benzyl phosphorous ylide obtained in-situ in presence of base to yield olefin (2b) with optical purity 99% ee and cis:trans isomeric ratio of 1:1.9;

c. methylating olefin (2b) with methyl iodide and NaH at 0 to 10° C. to obtain N-methylated olefin (3b);

d. deprotecting the N-Boc group followed by intramolecular FCC of N-methylated olefin in presence of polyphosphoric acid in solvent under reflux condition to obtain a mixture of (+)-tametraline [(+)-3] and its C4 epimer with syn:anti ratio of 1:1;

e. converting (+)-tametraline [(+)-3] and its C4 epimer to hydrochloride salt followed by separating the crystals of (+)-tametraline-D-(−)-mandelate selectively using D-(−)-mandelic acid.

In yet another embodiment, present invention provides an intermediates comprising:

a. (S)-tert-Butyl (3-oxo-1-phenylpropyl)carbamate;

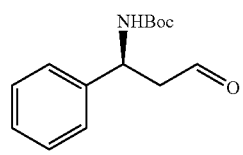 [SMILES: CC(C)(C)OC(=O)N[C@@H](CC=O)c1ccccc1]

b. tert-butyl (S)-(4-(3,4-dichlorophenyl)-1-phenylbut-3-en-1-yl)carbamate;

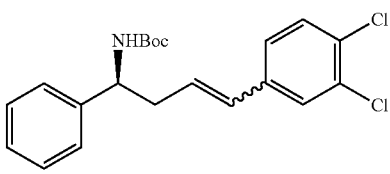 [SMILES: CC(C)(C)OC(=O)N[C@@H](CC=Cc1ccc(Cl)c(Cl)c1)c1ccccc1]

c. (S)-tert-butyl-(4-(3,4-dichlorophenyl)-1-phenylbut-3-en-1-yl(methyl) carbamate

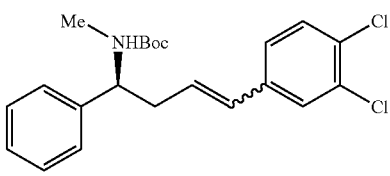

d. (R)-tert-buty-(1,4-diphenylbut-3-en-1-yl)(methyl)carbamate;

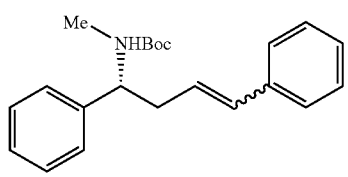

In yet another embodiment of the present invention, compound of formula I as prepared along with pharmaceutically acceptable excipients.

DETAILED DESCRIPTION OF THE INVENTION

Present invention provides a highly enantioselective synthesis of 1-amino aryl tetralin compound of formula (I), with high therapeutic value as antidepressants, using proline catalyzed Mannich reaction of suitable aldehyde as chirality inducing step.

The proline catalyzed Mannich reaction of aldehyde and acid catalyzed intramolecular Friedel-Crafts alkylation constitute the key steps in synthesis of 1-amino aryl tetralins, thus reducing the steps of synthesis and providing desired compounds with high enantioselectivity and provides the flexibility in arriving at desired diasteromers of biologically active amino-aryl tetralin compound of formula I.

Present invention provides a short, cost effective proline catalysed process for enantioselective synthesis of antidepressants 1-amino aryl tetralin compound of Formula (I)

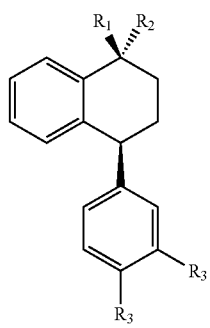

wherein
$R_1$ and $R_2$ independent of each other represent hydrogen, (un)substituted or substituted amine group;
$R_3$ and $R_4$ independent of each other represent hydrogen or halogen;
comprising the steps of:
a. reacting aryl N-Boc-imine with an aldehyde in presence of D or L-proline to obtain compound (1);
b. reacting compound (1) with triphenyl phosphonium salt in presence of n-butyl lithium or ᵗBuOK in dry THF to obtain olefinic carbamate (2);
c. alkylating carbamate (2) in presence of alkyl halide and NaH at 0 to 10° C. to obtain compound (3);
d. deprotecting the N-boc group of compound (3) followed by intramolecular FCC in presence of acid to afford desired compound of formula I. (FIG. 1)

The 1-amino aryl tetralines are obtained in diastereomeric ratio ranging between 1:1 to 1:3 (syn:anti).

They are converted to their hydrochloride salts or further treated with D-(−)-mandelic acid to obtain both syn and anti-isomer in quantitative yields selectively.

The process of the present invention affords synthesis of 1-amino-aryl tetralin compound of formula I selected from (+) sertraline and (+) tametraline with ee>95%.

The present invention provides short, cost effective proline catalysed enantioselective synthesis of (+) sertraline with ee>95%

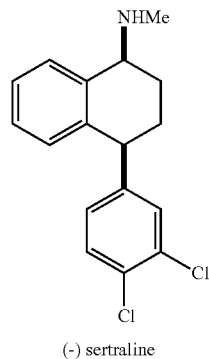 [SMILES: CN[C@H]1CC[C@@H](c2ccc(Cl)c(Cl)c2)c2ccccc21]

(−) sertraline comprising the steps of:
a. reacting N-Boc-benzaldimine with acetaldehyde in presence of L-proline to obtain (−)β-amino aldehyde (1a);
b. treating (−) β-amino aldehyde (1a) with semi stabilized 3,4-dichlorobenzyl phosphorous ylide obtained in-situ in presence of base to yield olefinic carbamate (2a) with optical purity 99% ee and cis: trans isomeric ratio of 1.3:1;
c. methylating olefinic carbamate (2a) with methyl iodide and NaH at 0 to 10° C. to obtain N-methylated olefin (3a);
d. deprotecting the Boc group of compound (3a) followed by intramolecular FCC of N-methylated olefin in presence of polyphosphoric acid in solvent under reflux condition to obtain mixture of (+) sertraline and its $C_4$ epimer with syn:anti ratio of 1:3;
e. converting (+) sertraline and its $C_4$ epimer seperated through coloumn chromatography and converting them to their hydrochloride salts respectively.

Accordingly, N-Boc-benzaldimine was subjected to L-proline catalyzed Mannich reaction with acetaldehyde to obtain β-aminoaldehyde (−)1a. Aldehyde (−)-1a was then treated with semistabilized 3,4-dichlorobenzyl phosphorous ylide [in situ derived from the reaction between 3,4-Cl$_2$C$_6$H$_3$CH$_2$PPh$_3$Br Wittig salt and n-BuLi or KO$^t$Bu] to obtain carbamate (2a) in 60% yield using n-BuLi as base or 71% yield using KO$^t$Bu as base. The optical purity of olefin 2a was found to be 99% ee with cis:trans isomeric ratio of 1.3:1 determined from chiral HPLC analysis. The olefin 2a was methylated using MeI and NaH at 0 to 10° C. to obtain N-methyl olefin (3a). The N-boc group was deprotected followed by intramolecular Friedel-Crafts alkylation of N-methylated olefin 1c in one pot by treatment with polyphosphoric acid in ethylene dichloride under reflux condition overnight to yield (+)-sertraline (+)1 (syn) and its C4 epimer (−)2 (anti) with syn:anti ratio of 1:3 after column chromatographic separation.

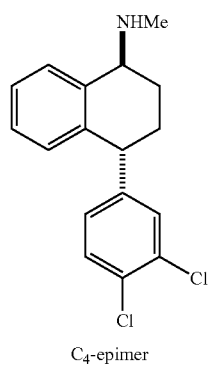

C$_4$-epimer

Further, (+)-sertraline (+)1 and its C$_4$-epimer (−)2 were converted into their hydrochloride salts by treating with dry HCl gas in dry Et$_2$O separately to obtain each of (+)-1. HCl and (−)-2. HCl selectively.

The olefin (2a) and its N-methyl olefin were characterized by NMR, IR and mass spectroscopy.

The present invention provides short, cost effective proline catalysed enantioselective synthesis of (+)-tametraline with ee>95%

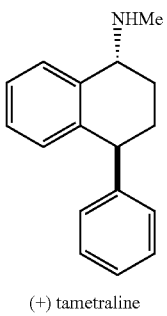 [SMILES: CN[C@@H]1CC[C@@H](c2ccccc2)c2ccccc21]

(+) tametraline comprising the steps of:
a. reacting N-Boc-benzaldimine with acetaldehyde in presence of D-proline to obtain (+) β-amino aldehyde (1b);
b. treating (−) β-amino aldehyde (1b) with semistabilized 3,4-dichlorobenzyl phosphorous ylide obtained in-situ in presence of base to yield olefinic carbamate (2b) with optical purity 99% ee and cis: trans isomeric ratio of 1:1.9;
c. methylating olefin of step (b) using methyl iodide and NaH at 0 to 10° C. to obtain N-methylated olefin (3b);
d. deprotecting the N-Boc group of N-methylated olefin (3b) as obtained in step (c) followed by intramolecular FCC of N-methylated olefin in presence of polyphosphoric acid in solvent under reflux condition to obtain a mixture of (+)-tametraline [(+)-3] and its C4 epimer with syn:anti ratio of 1:1;
e. converting (+)-tametraline [(+)-3] and its C$_4$ epimer to hydrochloride salt and separating the crystals of (+)-tametraline-D-(−)-mandelate selectively using D-(−)-mandelic acid;

Accordingly, β-aminoaldehyde (+)-1b was derived from Mannich reaction of acetaldehyde and N-Boc-benzaldimine using D-proline. This was treated with semi-stabilized benzyl phosphorous ylide [derived from C$_6$H$_5$CH$_2$PPh$_3$Br and n-BuLi] to provide the olefin (2b). The optical purity of olefin 2c was found to be 99% ee with cis:trans isomeric ratio of 1:1.9 determined from chiral HPLC analysis. The olefin 2b was treated with methyl iodide and NaH at 0 to 10° C. to yield N-methylated olefin (3b). The N-boc group was deprotected followed by subjecting the N-methylated olefin to intramolecular FCC in "one pot" by treating with polyphosphoric acid in ethylene dichloride as solvent under reflux condition for 12 h to yield a mixture of (+)-tametraline [(+)-3] and its C4 epimer. (+)-tametraline [(+)-3] and its C4 epimer was treated with dry HCl gas in dry Et$_2$O to obtain the hydrochloride salts respectively which were separated using D-(−)-mandelic acid to obtain the crystals of (+)-tametraline-D-(−)-mandelate selectively.

The olefin (2c) and its N-methyl olefin were characterized by NMR, IR and mass spectroscopy.

The present invention discloses novel intermediates comprising;

a. (S)-tert-Butyl (3-oxo-1-phenylpropyl)carbamate;

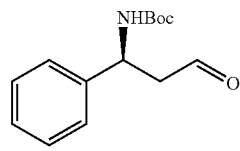 [SMILES: CC(C)(C)OC(=O)N[C@@H](CC=O)c1ccccc1]

b. tert-butyl (S)-(4-(3,4-dichlorophenyl)-1-phenylbut-3-en-1-yl)carbamate;

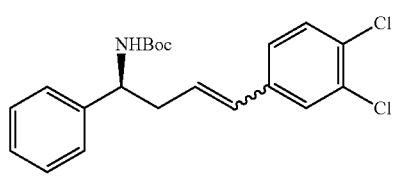 [SMILES: CC(C)(C)OC(=O)N[C@@H](CC=Cc1ccc(Cl)c(Cl)c1)c1ccccc1]

c. tert-butyl (S)-(4-(3,4-dichlorophenyl)-1-phenylbut-3-en-1-yl)(methyl)carbamate

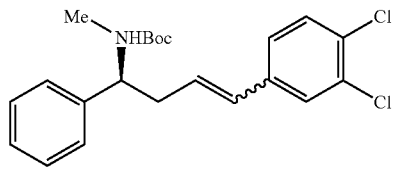

d. tert-buty-(R)-(1,4-diphenylbut-3-en-1-yl)(methyl)carbamate;

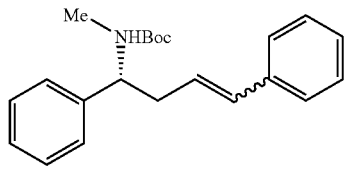

The present invention provides pharmaceutical composition comprising 1-amino aryl sertraline viz. (+) sertraline and (+) tametraline prepared by the process of current invention along with pharmaceutically acceptable excipients.

EXAMPLES

The following examples are given by way of illustration and therefore should not be construed to limit the scope of the invention.

Example 1

General Experimental Procedure for the Synthesis of (+)-Sertraline (i) (S)-tert-Butyl (3-oxo-1-phenylpropyl)carbamate

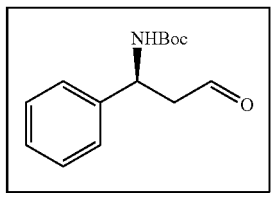 [SMILES: CC(C)(C)OC(=O)N[C@@H](CC=O)c1ccccc1]

To a stirred solution of aryl N-Boc-imine (1.4 mmol) and redistilled acetaldehyde (0.39 mL, 7 mmol) in CH$_3$CN (15 mL) at 0° C. was added L-proline (0.032 g, 20 mol %) and the mixture stirred further at 0° C. for 3 h. After the completion of reaction (monitored by TLC), it was quenched with water and extracted with Et$_2$O (3×50 mL). The combined organic layers were washed with brine, dried over anhyd. Na$_2$SO$_4$, filtered and concentrated under reduced pressure to give the crude aldehyde. Flash column chromatographic purification [silica gel (230-400 mesh) and pet. ether:EtOAc as an eluent] gave β-aminoaldehyde.

Yield: 55%; pale yellow solid; mp: 91-94° C., (lit.[33] mp: 92-93.5° C.); [α]$^D_{25}$ −30.10 (c, 1.15, CHCl$_3$); lit.[33] [α]$^D_{25}$ +29.0 (c, 1.4, CHCl$_3$) for its antipode; IR (CHCl$_3$, cm$^{-1}$): υ$_{max}$ 700, 1021, 1049, 1169, 1250, 1369, 1391, 1498, 1513, 1692, 2977, 3341; $^1$H NMR (200 MHz, CDCl$_3$): δ 1.41 (s, 9H), 2.83-2.96 (m, 2H), 4.87 (br s, 1H), 5.17 (br s, 1H), 7.26-7.34 (m, 5H), 9.73 (t, J=1.7 Hz, 1H); $^{13}$C NMR (50 MHz, CDCl$_3$): δ 28.3, 39.9, 49.9, 79.9, 126.3, 127.7, 128.8, 135.2, 155.0, 193.3, 199.8; Analysis: C$_{14}$H$_{19}$NO$_3$ requires C, 67.45; H, 7.68; N, 5.62. found: C, 67.32; H, 7.41; N, 5.46%.

(ii) (S)-tert-butyl-(4-(3,4-dichlorophenyl)-1-phenyl-but-3-en-1-yl)carbamate

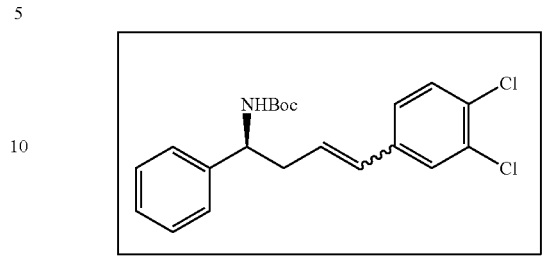

To a stirred solution of 3,4-dichlorobenzyl triphenylphosphonium bromide (1.3 equiv) in dry. THF kept at 0° C. added n-butyllithium (1.2 equiv, 1.6M solution in n-hexane) and allowed to stir for 30 min at the same temperature to generate the ylide. Then a solution of β-aminoaldehyde (1 equiv.) in dry. THF was added to the ylide and the reaction mixture was stirred for 1 h. After completion of reaction of reaction, it was quenched with sat.NH$_4$Cl solution. The combined organic layers were washed with brine, dried over anhyd. Na$_2$SO$_4$, filtered and concentrated under reduced pressure to give the crude olefin. Flash column chromatographic purification [silica gel (230-400 mesh) and pet. ether:EtOAc as an eluent] gave the desired carbamate.

Yield: 60%, yellow gum; [α]$^{25}_D$: −37.0 (c, 1.32, CHCl$_3$); IR (CHCl3, cm$^{-1}$): 628, 700.25, 830.4, 874.8, 1059, 1142, 1335, 1365, 1394, 1447.26, 1475, 1656, 3357; $^1$H NMR (CDCl$_3$, 200 MHz): 1.39 (s, 9H), 2.64-2.7 (m, 2H), 4.81-4.88 (m, 2H), 5.65-6.13 (m, 1H), 6.29-6.37 (m, 1H), 7.06-7.17 (dd, J=2.02, 8.34 Hz, 1H), 7.2-7.41 (m, 7H); $^{13}$C NMR (CDCl$_3$, 125 MHz): 28.42, 40.51, 54.62, 79.64, 125.3, 126.3, 127.5, 127.9, 128.03, 128.71, 130.17, 130.4, 130.8, 131.01, 133, 137.34, 155.1; Anal. Calcd for C$_{21}$H$_{23}$Cl$_2$NO$_2$ requires C, 64.29; H, 5.91; Cl, 18.01; N, 3.57. found: C, 64.5; H, 5.74; Cl, 18.35; N, 3.4%.

(iii) (S)tert-butyl-(4-(3,4-dichlorophenyl)-1-phenyl-but-3-en-1-yl)(methyl) carbamate

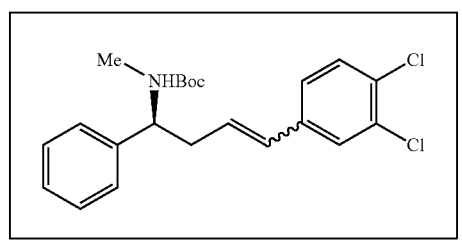

To a stirred solution of carbamate in anhydrous THF and DMF (4:1) was added NaH (1.5 equiv, 60% in mineral oil) at 0° C. After stirring for 30 min, CH$_3$I (2.5 equiv) was added at 0° C. under N$_2$. The reaction mixture was stirred at room temperature for 6 h under N$_2$ and quenched with H$_2$O (10 mL). The aqueous layer was extracted with EtOAc (2×25 mL). The organic layer was washed with brine, dried over Na$_2$SO$_4$, and concentrated in vacuo. The residue was purified by flash column chromatography (n-hexane/EtOAc=97/3) to afford 3 in 95% yield: Yield: 95%, pale yellow viscous liquid; [α]$^{25}_D$: −37.0 (c, 1.32, CHCl$_3$); IR (CHCl3, cm$^{-1}$): 565.3, 598.34, 627.4, 698.8, 737, 765.3, 826.3, 874, 950.9, 1028.8, 1138.8, 1255.8, 1324.77, 1365.5, 1389.5, 1447.33, 1473.4, 1682, 2928, 2975; $^1$H NMR (CDCl$_3$, 200 MHz): 1.43-1.49 (br s, 9H), 2.46-2.6 (br s, 3H), 2.75-2.9 (m, 2H), 5.39-5.51 (br s, 1H), 5.6-6.46 (m, 1H), 6.36-6.46 (m, 1H), 7.11-7.43 (m, 8H); $^{13}$C NMR (CDCl$_3$, 125 MHz): 28.25, 28.46, 29.41, 33.8, 57.48, 60.77, 79.66, 124.77, 125.17, 127.3, 127.38, 127.8, 127.86, 128.42, 128.63, 129.07, 129.8, 130.15, 130.26, 130.42, 131.15, 132.36, 132.55, 137.24, 137.45, 139.55, 139.69, 155.94; Anal. Calcd for $C_{22}H_{25}Cl_2NO_2$ requires C, 65.03; H, 6.2; Cl, 17.45; N, 3.45. found: C, 65.32; H, 6.46; Cl, 17.35; N, 3.57%.

(iv) (1S)-4-(3,4-dichlorophenyl)-N-methyl-1,2,3,4-tetrahydronaphthalen-1-amine hydrochloride

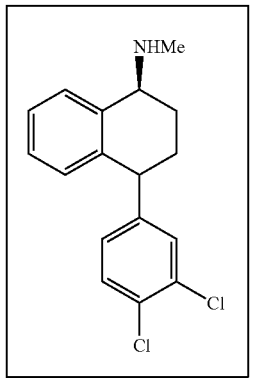 [SMILES: CN[C@H]1CCC(c2ccc(Cl)c(Cl)c2)c2ccccc21]

A solution of 3 (1 equiv) dissolved in 1,2-dichloroethane was added to movable liquid of polyphosphoric acid (liquefied after heating the neat polyphosphoric acid at 80° C.). The above reaction mixture was stirred overnight at 90° C. Then 1,2-dichloroethane was removed under vacuo and quenched with sat.NaHCO$_3$ solution. The aqueous layer was extracted with EtOAc. The organic layer was washed with brine, dried over Na$_2$SO$_4$, and concentrated in vacuo. The residue was purified by flash column chromatography using neutralized silica gel with Et$_3$N (n-hexane/EtOAc=97/10) to afford amine in 82% yield.

Yield: 84% (dr=1:3, of syn:anti), yellow oil; For syn isomer: $^1$H NMR (500 MHz, CDCl$_3$) δ 1.25 (br s, 1H), 1.85-2.15 (m, 4H), 2.55 (s, 3H), 3.81 (m, 1H), 3.97-3.99 (dd, J=9.16, 6.1 Hz, 1H), 6.79-6.8 (d, J=7.6 Hz, 1H), 6.98-7.0 (dd, J=8.24, 1.83 Hz, 1H), 7.1-7.13 (m, 1H), 7.18-7.21 (m, 1H), 7.26-7.27 (m, 1H), 7.33-7.35 (d, J=8.24 Hz, 1H), 7.38-7.39 (d, J=7.6 Hz, 1H); $^{13}$C NMR (100 MHz, CDCl$_3$) δ 23.99, 28.78, 32.4, 44.19, 56.84, 127.05, 127.84, 128.02, 128.94, 129.67, 130.28, 130.3, 130.43, 130.57, 136.32, 138.58, 147.08;

Anti isomer: $^1$H NMR (500 MHz, CDCl$_3$) δ 1.62 (br s, 1H), 1.74-1.78 (m, 2H), 1.93-2.38 (m, 2H), 2.51 (s, 3H), 3.78-3.8 (m, 1H), 4.12-4.14 (m, 1H), 6.82-6.85 (m, 2H), 7.11-7.14 (m, 2H), 7.21-7.26 (m, 1H), 7.31-7.32 (d, J=8.24 Hz, 1H), 7.44-7.46 (d, J=7.6 Hz, 1H); $^{13}$C NMR (125 MHz, CDCl$_3$) δ 24.53, 28.71, 33.85, 44.28, 57.05, 126.75, 127.12, 128.11, 128.59, 129.92, 130.07, 130.11, 130.56, 132.18, 138.02, 139.52, 147.51;

(v) (1S,4S)-4-(3,4-dichlorophenyl)-N-methyl-1,2,3,4-tetrahydronaphthalen-1-amine hydrochloride

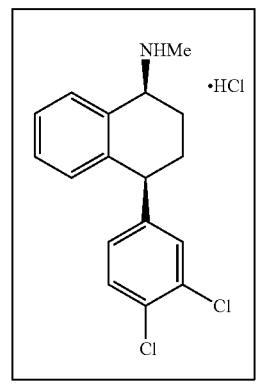 [SMILES: CN[C@H]1CC[C@@H](c2ccc(Cl)c(Cl)c2)c2ccccc21 ; Cl]

Yield: 94%, white solid; 1H NMR (400 MHz, CDCl$_3$) δ 2.04-2.39 (m, 4H), 2.57 (s, 3H), 3.97-4.00 (m, 1H), 4.3 (m, 1H), 6.85-6.87 (d, J=7.6 Hz, 1H), 7.16-7.25 (m, 3H), 7.34-7.4 (m, 2H), 7.75-7.76 (d, J=7.05 Hz, 1H), 9.87-9.99 (m, 2H); $^{13}$C NMR (100 MHz, CDCl$_3$) δ 23.08, 27.63, 29.6, 44.99, 56.27, 127.5, 128.6, 129.6, 129.7, 130.4, 130.5, 130.7, 130.9, 131.3, 132.58, 139.9, 145.1;

Example 2

General Experimental Procedure for the Synthesis of Tametraline

The same experimental procedure was followed for tametraline synthesis as shown for the above compounds.

(R)-tert-butyl-(1,4-diphenylbut-3-en-1-yl)carbamate

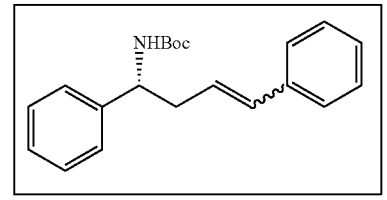 [SMILES: CC(C)(C)OC(=O)N[C@H](CC=Cc1ccccc1)c1ccccc1]

Yield: 58%, pale yellow gum; 1H NMR (CDCl$_3$, 200 MHz): 1.39 (s, 9H), 2.67-2.78 (m, 2H), 4.78-4.87 (m, 2H), 5.55-6.13 (m, 1H), 6.3-6.55 (m, 1H), 7.15-7.4 (m, 10H); $^{13}$C NMR (CDCl$_3$, 125 MHz): 28.42, 35.78, 40.56, 54.81, 79.44, 125.5, 126.2, 126.3, 126.35, 126.85, 127.23, 127.75, 128.24, 128.55, 128.74, 128.94, 129.9, 131.61, 133.23, 137.14, 142.39, 155.1; Anal. Calcd for $C_{21}H_{25}NO_2$ requires C, 77.98; H, 7.79; N, 4.33. found: C, 78.06; H, 7.9; N, 4.56%.

(R)-tert-butyl-(1,4-diphenylbut-3-en-1-yl)(methyl)carbamate

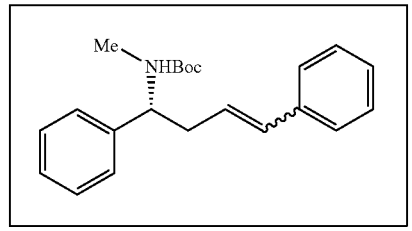

Yield: 94%, pale yellow viscous liquid; 1H NMR (CDCl$_3$, 200 MHz): 1.42-1.49 (br s, 9H), 2.45-2.59 (br s, 3H), 2.8-2.95 (m, 2H), 5.38 (m, 1H), 5.6-6.23 (m, 1H), 6.45-6.55 (m, 1H), 7.14-7.34 (m, 10H); $^{13}$C NMR (CDCl$_3$, 125 MHz): 28.21, 28.39, 29.35, 33.6, 57.48, 60.77, 79.66, 125.42, 126.15, 126.28, 126.81, 127.32, 127.64, 128.38, 128.47, 128.74, 128, 129.89, 131.64, 133.18, 137.21, 142.35, 155.42; Anal. Calcd for C$_{22}$H$_{27}$NO$_2$ requires C, 78.3; H, 8.06; N, 4.15. found: C, 78.71; H, 8.17; N, 4.45%.

(1R,4S)—N-methyl-4-phenyl-1,2,3,4-tetrahydronaphthalen-1-amine

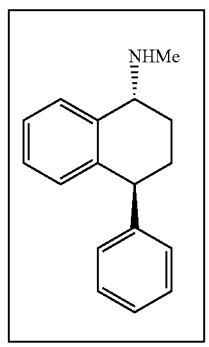 [SMILES: CN[C@@H]1CC[C@@H](c2ccccc2)c2ccccc21]

Yield: 83% (dr=1:1, of syn:anti), yellow oil; Anti isomer: $^1$H NMR (200 MHz, CDCl$_3$) δ 1.6 (br s, 1H), 1.78-2.16 (m, 4H), 2.52 (s, 3H), 4.03-4.08 (m, 1H), 4.15-4.2 (m, 1H), 6.85-7.61 (m, 9H); $^{13}$C NMR (125 MHz, CDCl$_3$) δ 28.4, 29.8, 34.93, 46.86, 59.74, 126.9, 127.84, 128.56, 129.23, 129.81, 130.37, 130.98, 132.26, 138.46, 139.38, 143.16;

ADVANTAGES OF INVENTION

Commercially available D or L-Proline as cheap catalyst.
Cheap and simple starting materials.
High yielding process with excellent enantio-selectivity and diastereomeric ratio of syn:anti 1:3 (for sertraline), and 1:1 (for tametraline).
The route comprises of only four steps as compared to already reported methods.

We claim:
1. A process for the enantioselective synthesis of a 1-amino aryl tetralin compound of Formula (I):

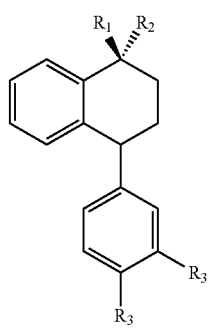

Formula (I)

wherein:
one of R$_1$ and R$_2$ is hydrogen and the other is unsubstituted amine; and
R$_3$ is hydrogen or halogen;
the process comprising the steps of;

a. reacting N-Boc-benzaldimine with acetaldehyde in the presence of D or L-proline to obtain a compound 1:

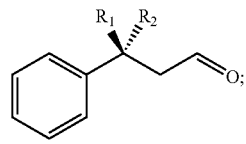

b. reacting compound 1 with a triphenyl phosphonium salt in presence of n-butyl lithium or $^t$BuOK in dry THF to obtain an olefinic carbamate compound 2:

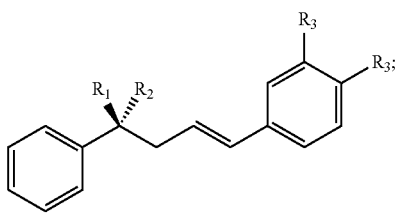

c. alkylating the olefinic carbamate compound 2 in the presence of alkyl halide and NaH at 0 to 10° C. to obtain compound 3, wherein the unsubstituted amino group is alkylated; and

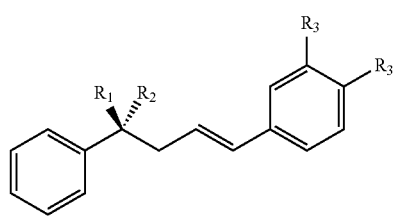

d. deprotecting the N-Boc group of compound 3, followed by an intramolecular FCC (Friedel-Crafts intramolecular cyclization) in the presence of acid to afford the compound of Formula (I).

2. The process as claimed in claim 1, wherein the compound of Formula (I) is (+) sertraline or (+) tametraline

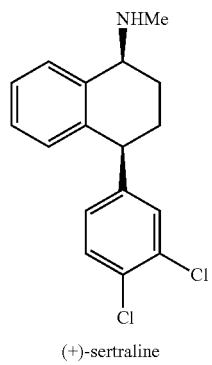

(+)-sertraline

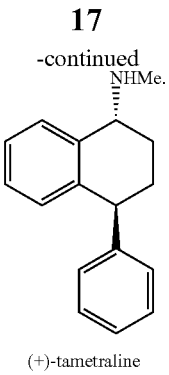

(+)-tametraline

3. The process as claimed in claim 1, wherein (+)-sertraline is prepared with ee>95%

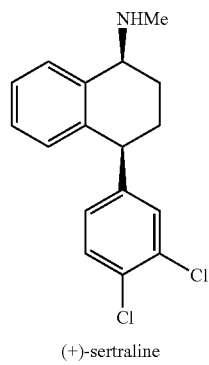 [SMILES: CN[C@H]1CC[C@@H](c2ccc(Cl)c(Cl)c2)c2ccccc21]

(+)-sertraline and the process comprises the steps of:
  a. reacting N-Boc-benzaldimine with acetaldehyde in the presence of L-proline to obtain (−)-β-amino aldehyde (1a):

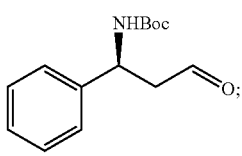

(1a)

b. treating (−)-β-amino aldehyde (1a) with semistabilized 3,4-dichlorobenzyl phosphorous ylide, obtained in-situ, in presence of a base to yield carbamate (2a):

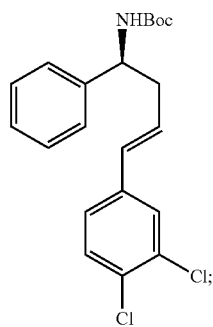

(2a)

c. methylating carbamate (2a) using methyl iodide and NaH at 0 to 10° C. to obtain N-methylated olefin (3a);

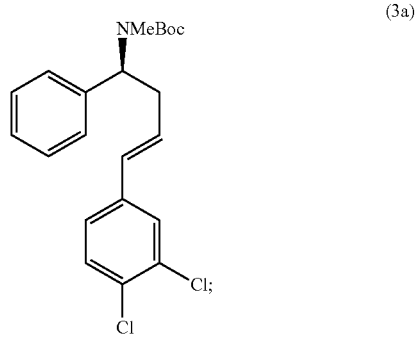

(3a)

d. deprotecting the Boc group, followed by intramolecular FCC of the N-methylated olefin in the presence of polyphosphoric acid in a solvent under reflux conditions to obtain a mixture of (+)-sertraline and its $C_4$-epimer (−)-2 with a syn: anti ratio of 1:3 and
  e. separating the (+)-sertraline and the $C_4$-epimer (−)-2 using column chromatography, followed by converting to the respective hydrochloride salt.

4. The process as claimed in claim 1, wherein (+)-tametraline is prepared with ee>95% and comprises the steps of:
  a. reacting N-Boc-benzaldimine with acetaldehyde in the presence of D-proline to obtain (+)-β-amino aldehyde (1b):

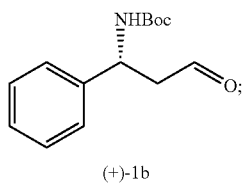 [SMILES: CC(C)(C)OC(=O)N[C@H](CC=O)c1ccccc1]

(+)-1b b. treating (+)-β-amino aldehyde (1b) with semistabilized benzyl phosphorous ylide, obtained in-situ, in the presence of a base to yield olefin (2b) with an optical purity of 99% ee and a cis: trans isomeric ratio of 1:1.9:

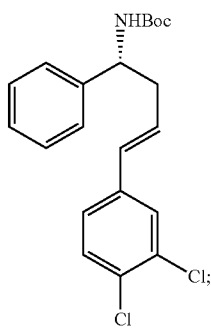

2b c. methylating olefin (2b) with methyl iodide and NaH at 0 to 10° C. to obtain N-methylated olefin (3b):

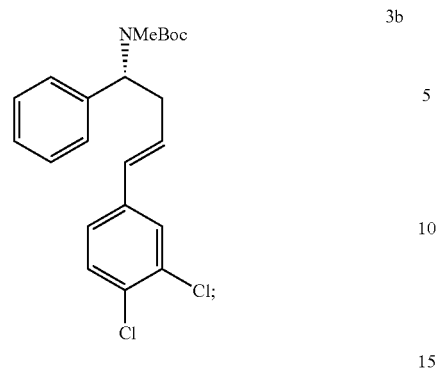

d. deprotecting the N-Boc group, followed by intramolecular FCC of the N-methylated olefin in the presence of polyphosphoric acid in a solvent under reflux conditions to obtain a mixture of (+)-tametraline [(+)-3] and its $C_4$ epimer with a syn:anti ratio of 1:1 and e. converting the (+)-tametraline [(+)-3] and its $C_4$ epimer to the respective hydrochloride salt, followed by separating the crystals of (+)-tametraline-D-(−)-mandelate selectively using D-(−)-mandelic acid.

* * * * *